(12) United States Patent
Sumian et al.

(10) Patent No.: US 8,123,940 B2
(45) Date of Patent: Feb. 28, 2012

(54) FILTRATION UNIT FOR THE SELECTIVE ELIMINATION OF A TARGET SUBSTANCE

(75) Inventors: Chryslian Sumian, Lambersart (FR); David Godard, Tourcoing (FR)

(73) Assignee: Maco Pharma, Mouvaux (FR)

( * ) Notice: Subject to any disclaimer, the term of this patent is extended or adjusted under 35 U.S.C. 154(b) by 0 days.

(21) Appl. No.: 12/100,175

(22) Filed: Apr. 9, 2008

(65) Prior Publication Data

US 2008/0223776 A1    Sep. 18, 2008

Related U.S. Application Data

(63) Continuation of application No. PCT/FR2006/002240, filed on Oct. 5, 2006.

(30) Foreign Application Priority Data

Oct. 10, 2005 (FR) ..................... 05 53069

(51) Int. Cl.
*B01D 29/56* (2006.01)
*B01D 15/34* (2006.01)

(52) U.S. Cl. ............. 210/257.1; 210/266; 210/283; 210/483; 210/488; 210/489; 210/490; 210/491; 210/501; 210/502.1; 210/503; 210/504; 210/505

(58) Field of Classification Search ............ 210/257.1, 210/266, 283, 483, 488, 489, 490, 491, 501, 210/502.1, 503, 504, 505
See application file for complete search history.

(56) References Cited

U.S. PATENT DOCUMENTS

| | | | | |
|---|---|---|---|---|
| 4,033,881 A | * | 7/1977 | Pall | 210/491 |
| 4,828,698 A | * | 5/1989 | Jewell et al. | 210/266 |
| 5,169,528 A | * | 12/1992 | Karbachsch et al. | 210/264 |
| 5,290,446 A | * | 3/1994 | Degen et al. | 210/489 |
| 5,454,946 A | * | 10/1995 | Heagle et al. | 210/503 |
| 5,472,600 A | * | 12/1995 | Ellefson et al. | 210/317 |
| 5,639,376 A | | 6/1997 | Lee | 210/645 |
| 7,140,497 B2 | | 11/2006 | Verpoort | 210/507 |

FOREIGN PATENT DOCUMENTS

| | | |
|---|---|---|
| EP | 0526678 | 2/1993 |
| EP | 1382361 | 1/2004 |
| WO | WO 00/74806 | 12/2000 |
| WO | WO 2004/090102 | 10/2004 |

OTHER PUBLICATIONS

International Search Report, PCT/FR2006/002240, Feb. 7, 2007.

* cited by examiner

*Primary Examiner* — John Kim
(74) *Attorney, Agent, or Firm* — Baker Botts L.L.P.

(57) ABSTRACT

A filtration unit for the selective elimination of a target substance from a biological fluid comprising an external envelope, wherein the envelope encloses a filtering medium comprising: an upstream structure for eliminating at least the target substance comprising a stack of layers that are arranged to allow the flow of fluid through the layers in one direction comprising a non-woven material, and particles interposed between at least some of the layers, wherein the particles have an affinity for the target substance; and a downstream structure for retaining the particles comprising at least one layer of porous material.

20 Claims, 3 Drawing Sheets

FILTRATION UNIT FOR THE SELECTIVE ELIMINATION OF A TARGET SUBSTANCE

CROSS-REFERENCE TO RELATED APPLICATIONS

This application is a continuation of International Application No. PCT/FR2006/002240 filed Oct. 5, 2006, which designates the United States and which is hereby incorporated by reference herein.

FIELD OF THE INVENTION

The invention relates to a filtration unit for the selective elimination of a target substance present in a biological fluid, as well as a pouch system comprising such a filtration unit.

It applies typically to the case where the target substance is an undesirable infectious agent such as a virus, prion protein, bacterium or parasite, or an exogenous substance used in a method of inactivating pathogens in a biological fluid intended to be transfused to a patient.

BACKGROUND

The prion is the agent responsible for transmissible spongiform subacute encephalopathies, in particular human variant CJD. Recent studies have shown that there exists a probable risk of transmission of the prion during blood transfusions. It therefore appears necessary to eliminate the infectious risk related to the prion from blood products intended to be transfused, in the same way as other pathogenic agents.

In the document WO-2004/090102, adsorbent particles in the form of resin capable of selectively binding the prion proteins present in the blood is described. These adsorbent particles are placed in columns.

Likewise, it is now recognized that the substances such as methylene blue or derivatives of psoralen used during the inactivation treatment of blood pathogens must be eliminated from blood products before they are transfused to a patient.

To this end, the document WO-00/74806 describes filtration devices including adsorbent particles such as activated carbon or polystyrene-based resins for eliminating pathogen inactivation substances from blood. These devices are also arranged in the form of columns containing the adsorbent particles.

It appears necessary to improve this type of filtration device comprising adsorbent particles in order in particular to comply with the particular blood filtration constraints, for example in terms of salting-out of the particles in the filtrate, speed of filtration and/or haemolysis of the red corpuscles. It is also important to have available filtration devices able to be easily manufactured, without loss of particles, and sterilized.

The invention therefore aims to propose a filtration unit that meets these requirements and that makes it possible to substantially eliminate a target substance present in the biological fluid whilst leaving the composition of the biological fluid substantially unchanged after filtration.

SUMMARY OF THE INVENTION

To this end and according to a first aspect, the invention relates to a filtration unit for the selective elimination of a target substance from a biological fluid, such as blood or a blood component, comprising an external envelope provided with at least one inlet orifice and at least one outlet orifice between which the fluid to be filtered flows in one direction, the envelope enclosing a filtering medium comprising, stacked from upstream to downstream:

an upstream structure for eliminating at least the target substance, the said structure comprising a stack of layers with a mean diameter D that is arranged to allow the flow of fluid through the said layers in the direction of flow, the said structure also comprising, interposed between at least some of the layers of the upstream structure, particles with a mean diameter greater than the diameter D, the said particles having an affinity for the target substance;

a downstream structure for retaining the particles that is formed from at least one layer of porous material, the mean diameter of the pores of the said material being less than or equal to the diameter D.

According to a second aspect, the invention relates to a pouch system for the selective elimination of a target substance from a biological fluid, such as blood or a blood component, comprising a pouch for collecting filtrate, the said pouch being connected, by means of a tube and an inlet orifice, to an outlet orifice of a filtration unit according to the first aspect of the invention.

BRIEF DESCRIPTION OF THE DRAWINGS

The invention will be understood by means of the following description with reference to the accompanying drawings, illustrating various embodiments.

DETAILED DESCRIPTION

In the following description, the terms "upstream" and "downstream" are defined with respect to the direction of flow of the fluid in the filtration unit, represented by the arrow "d" in FIG. 1.

Figure 1:
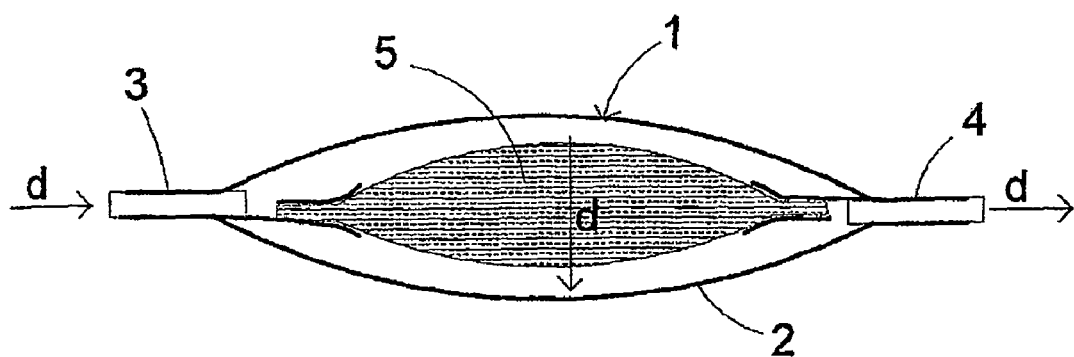
FIG. 1 schematically depicts a view of a section of a filtration unit according to one embodiment of the invention.

In relation to FIG. 1, the invention proposes a filtration unit 1 for the selective elimination of a target substance from a biological fluid, such as blood or a blood component. In particular, the biological fluid is whole blood, a plasma, a serum, a concentrate of red corpuscles or a platelet suspension. For example, the biological fluid comprises a whole blood or a red corpuscle concentrate previously leucodepleted. According to another example, the biological fluid is a serum of animal origin, used in cell culture media.

The target substance to be eliminated from the biological fluid is a pathogenic or infectious agent such as a virus, bacterium, parasite, fungus or prion protein. When the biological fluid is intended to be transfused to a patient, it is necessary to eliminate the infectious agent from this fluid in order to avoid contaminating the patient. This is particularly true in the case of the abnormal prion protein ($PrP^{SC}$), responsible for human variant CJD.

In a variant, the target substance is a substance for inactivating pathogens. Such substances are for example photosensitive agents such as phenothiazines, in particular methylene blue, psoralen or porphyrin derivatives, or chemical agents such as ethylene imines. These substances may be toxic when they are injected in a patient and must also be eliminated from the biological fluid intended to be transfused.

The elimination of the target substance may either be total or partial, so long as it is sufficient to eliminate or reduce the infectious risk relating to the infectious agents, and/or eliminate or reduce the toxicity of the inactivation substances, to a level that is acceptable for transfusion.

According to FIG. 1, the filtration unit 1 comprises an external envelope 2 provided with at least one inlet orifice 3 and at least one outlet orifice 4, between which the fluid to be filtered flows in a direction (d).

The envelope 2 is flexible, rigid or semi-rigid. In particular, when the envelope is flexible, the filtration unit is of the type described in the document EP-A-0 526 678.

Figure 2:
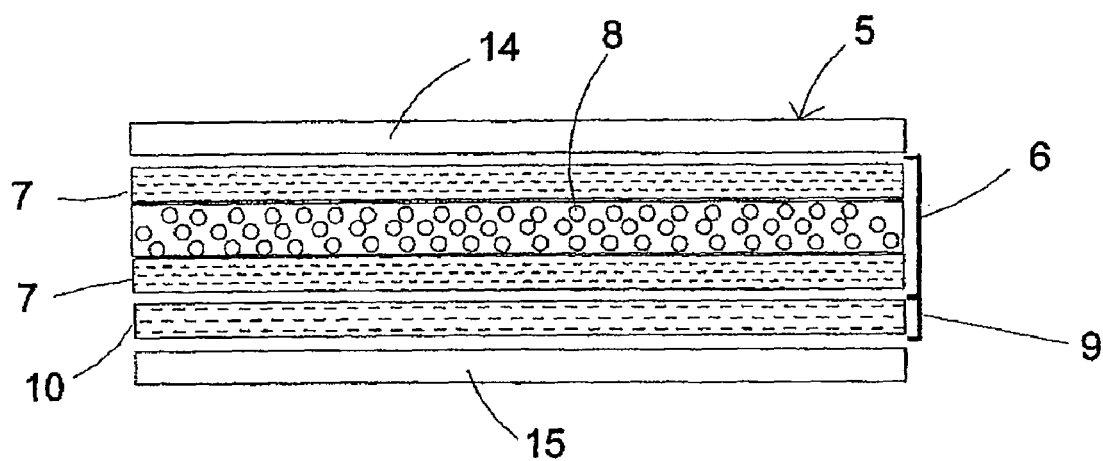
FIGS. 2 to 6 schematically depicts various embodiments of the filtering medium of a filtration unit according to the invention.

In relation to FIG. 2 and according to a first aspect of the invention, the envelope encloses a filtering medium 5 comprising, stacked from upstream to downstream:

an upstream structure 6 for eliminating at least the target substance, the said structure comprising a stack of layers 7 produced from a non-woven material having pores with a mean diameter D that is arranged to allow direction of flow, the said structure also comprising, interposed between at least some of the layers of the upstream structure, particles 8 with a mean diameter greater than the diameter D, the said particles having an affinity for the target substance; and a downstream structure 9 for retaining the particles that is formed from at least one layer of porous material 10, the mean diameter of the pores of the said material being less than or equal to the diameter D.

The upstream structure 6 allows the elimination from the biological fluid of at least one target substance, in particular the abnormal prion protein, while allowing the other components of the biological fluid to pass.

When the biological fluid is blood or a blood component, the stack of layers 7 of a non-woven material forms a so called in-depth filter, particularly suited since it allows the components of the blood, such as red corpuscles, to flow with a reduced risk of clogging and blocking of the filtering medium.

In particular, the layers 7 of non-woven material have a mean diameter D greater than or equal to 8 μm. This mean porosity is adapted to the case where the biological fluid comprises red corpuscles.

The layers 7 of the upstream structure 6 have identical or different mean pore diameters. Advantageously, the layers of the upstream structure 6 form a pore diameter gradient decreasing in the direction of flow of the fluid, so as to prevent clogging of the filtration unit 1.

The elimination of the target substance is carried out at least partially by means of the particles 8, which are capable of bonding by affinity to at least one infectious agent such as a virus, bacterium, parasite, fungus and prion protein, and/or to an exogenous inactivation substance.

According to a variant, the particles 8 have an affinity for more than one target substance, thus allowing the simultaneous elimination of several target substances from a biological fluid.

The particles are in particular adsorbent particles, such as particles of activated carbon, aluminum oxide, silica, or based on polymer such as polystyrene or polymethyl methacrylate.

Advantageously, these particles 8 are treated physically and/or chemically in order to improve their specificity and/or their affinity for the target substance or substances.

According to a particular embodiment, the layers 7 of the upstream structure 6 are arranged to eliminate part of the target substance by adsorption and/or filtration.

This is because, according to the physical and chemical characteristics of the layers 7 of non-woven material and their arrangement in the filtration unit 1, the target substance is filtered and/or adsorbed partially by the layers 7 of the upstream structure 6, thus increasing the retention capacity of the target substance of the filtration unit compared with the retention capacity of the particles 8 alone, as arranged in a column.

This elimination by adsorption and/or filtration is added to the elimination of the target substance by bonding to the particles 8.

For example, recent studies have shown that leucodepletion filters are capable of eliminating some of the prion proteins present in the blood or blood components (Luisa Gregori, Lancet, vol. 364, August 2004).

According to another embodiment, the upstream structure 6 is arranged to eliminate, by adsorption and/or by filtration, at least one other component of the biological fluid.

For example, when the layers 7 of the upstream structure 6 are identical or similar to those used in a leucodepletion filter, the filtration unit 1 makes it possible to eliminate both the target substance and the leucocytes from the biological fluid. A single filtration step is then necessary to eliminate two undesirable substances from a biological fluid intended to be transfused to a patient.

According to FIG. 2, the particles 8 are interposed between at least some of the layers 7 of the upstream structure 6, that is to say the upstream structure comprises at least two layers 7 of non-woven material between which the particles 8 are interposed.

According to a first embodiment, the particles 8 are disposed between the layers 7, that is to say they are not immobilized on the fibers of the layers 7.

For example, when the filtration unit is manufactured, a first layer of non-woven material is covered with particles, by means of a particle distributor, and then a second layer of non-woven material is stacked on the first layer covered with the particles, so as to form a sandwich comprising particles.

The term "sandwich" designates two layers 7 of non-woven material of the upstream structure 6 between which the particles 8 are disposed.

This manufacturing method is easily implemented since it requires no particular treatment of the particles and/or of the layers in order to bind or adhere the particles to the fibers of the layers.

Figure 3:
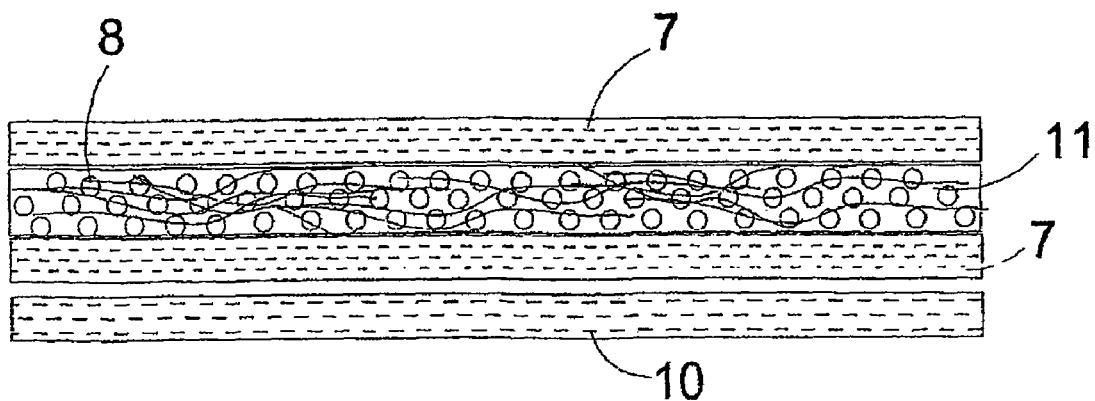

According to a second embodiment depicted in FIG. 3, the particles 8 are fixed to at least one layer 11 produced from non-woven material. The fixing is generally achieved by functionalization of the particles and/or of the fibers in order to immobilize the particles on the fibers constituting the layer 11.

In this case, the layer 11 of fibers/particles is interposed between two layers 7 of non-woven material in order to form the sandwich comprising the particles integrated in a fibrous grid.

The particles 8 have a mean diameter greater than the mean diameter of the layers 7 of non-woven material forming the upstream structure. According to a particular embodiment, the particles 8 are formed from balls of resin with a diameter of between 20 and 150 μm.

If the filtration unit 1 is intended to eliminate the prion proteins of a biological fluid, the particles 8 are, for example, those described in the document WO-2004/090102 and available under the commercial reference Toyopearl™ Amino 650M.

The total quantity of particles 8 present in the filtration unit depends on the retention capacity of the particles 8 and layers 7.

According to a particular embodiment, the quantity of particles between two layers is between 4 and 40 mg/cm$^2$. Thus the particles remain sufficiently dispersed between the two layers in order to allow the biological fluid to pass.

This is because an excessively large quantity of particles reduces the total porosity of the sandwich, which may slow the flow of biological fluid in the filtration unit.

Figure 4:
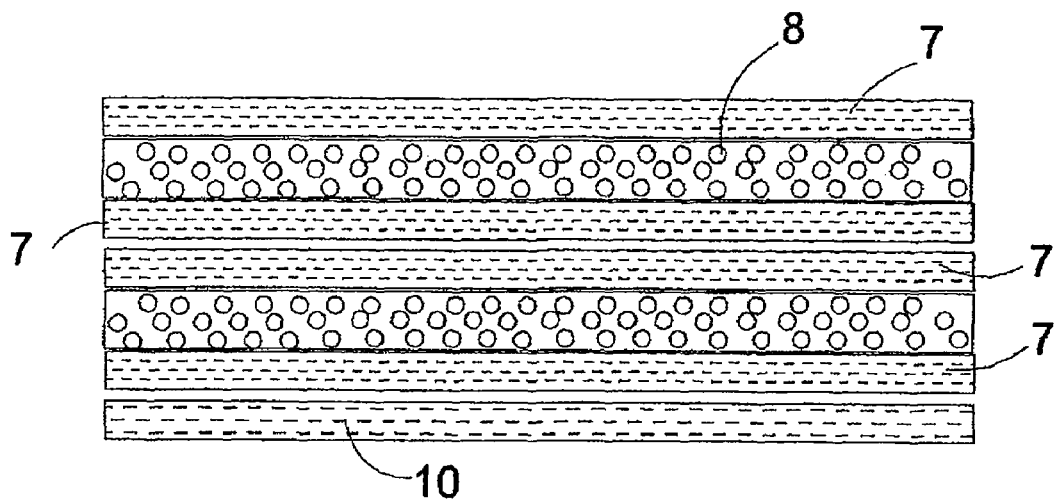

As depicted in FIG. 4, in order to increase the quantity of particles 8 in the filtration unit without increasing the quantity of particles between two layers 7, the number of sandwiches is increased in the filtration unit.

According to one embodiment, the number of sandwiches in the filtration unit is between 2 and 20, in particular 6.

Figure 5:
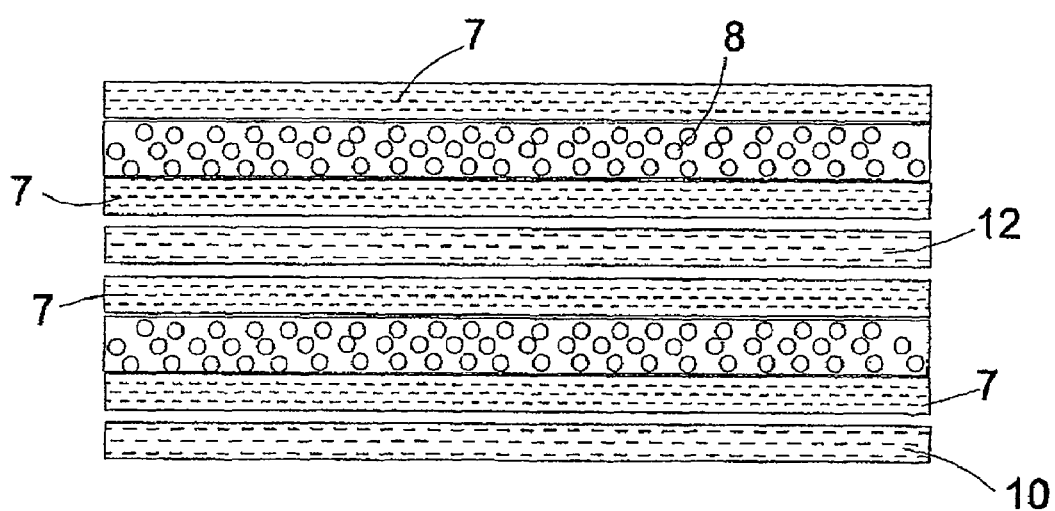

In relation to FIG. 5, one or more intermediate layers of porous material 12 are interposed between the layers 7 forming the sandwiches.

By controlling the characteristics of the one or more intermediate layers of porous material 12, such as their nature or porosity, it is possible in particular to regulate the speed of flow of the fluid in the filtration unit 1 and therefore the contact time between the fluid and the particles 8.

In a particular embodiment, these one or more intermediate layers of porous material 12 have a mean pore diameter greater than the porosity of the sandwiches comprising the particles 8.

These one or more intermediate layers of porous material 12 then fulfill the role of flow distributor and facilitate the flow of fluid in the filtration unit, that is to say they prevent a drop in the rate of flow of the fluid in the filtration unit due to the increase in the number of layers 7 and the quantity of particles 8.

For example, if the sandwich is composed of layers 7 of non-woven porous material with a mean diameter of approximately 12 μm, the porosity of the one or more intermediate layers of porous material 12 is approximately 12 μm.

In a variant of this example, the one or more intermediate layers of porous material are produced from a woven or molded thermoplastic material, in particular in the form of a grid.

According to another embodiment, the one or more intermediate layers of porous material 12 have a pore diameter less than or equal to the porosity of the sandwiches comprising the particles.

In this case, the intermediate layers slow down the flow of fluid in the filtration unit, which involves a longer contact time between the biological fluid and the particles.

According to a third embodiment, the one or more intermediate layers of porous material 12 are arranged so as to eliminate another blood component from the biological fluid, for example the leucocytes.

The increase in the number of layers 7 may however give rise to manufacturing difficulties during the incorporation of these layers in the external envelope of the filtration unit.

Figure 6:
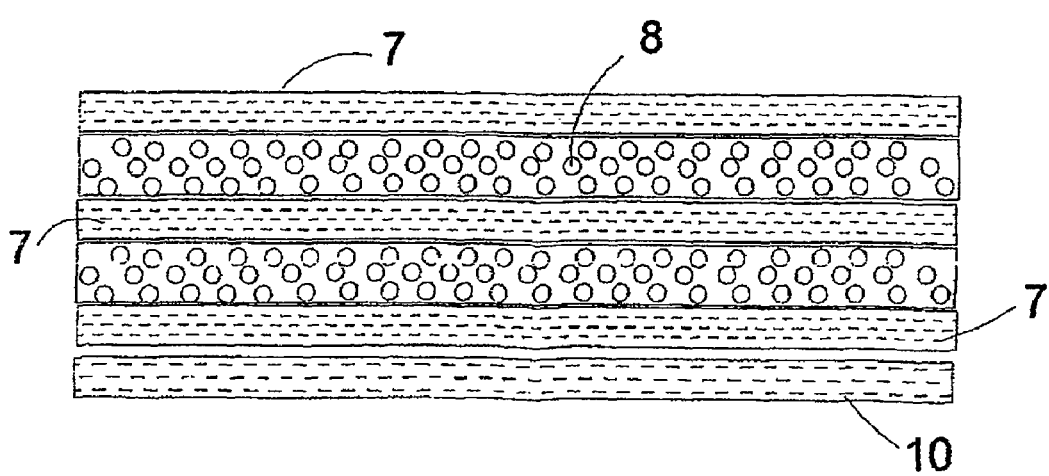
Figure 7:
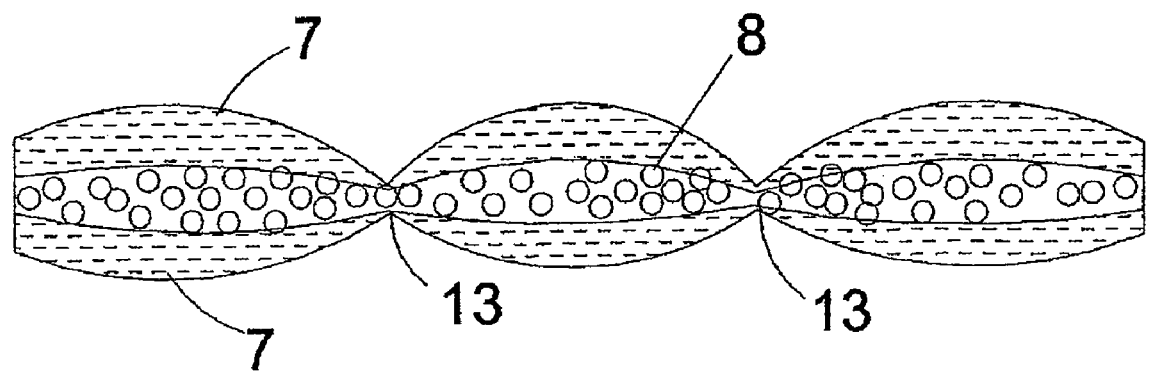
FIG. 7 schematically depicts two layers of non-woven material of the upstream structure of a filtration unit according to the invention, fixed between them by discrete welds.

To resolve this difficulty and to reduce the number of layers 7 in the filtration unit whilst keeping the same quantity of particles 8 between the layers 7, provision is made, as shown in FIG. 6, to alternate layers 7 with the layer of particles 8.

Thus the total number of layers 7 is reduced with respect to a stack of sandwiches, which facilitates the manufacture of the filtration unit 1.

It is also advantageous, for better elimination of the target substance, to distribute the particles 8 evenly between the layers 7.

To keep this even distribution during the manufacture and use of the filtration unit 1, and as illustrated in FIG. 7, at least two layers 7 are welded discretely to each other, so as to retain the particles between the said layers. This way of welding makes it possible to keep the two layers 7 enclosing the particles 8 fixed to each other.

For example, the two layers 7, between which the particles are interposed, are welded by heat or ultrasound by means of a calender that presses the layers hot at points separated from one another at regular intervals, so as to create discrete welding points 13.

This type of welding by embossing leaves the porosity of the layers 7 of non-woven material unchanged between the welding points 13.

According to one embodiment, the peripheries of at least two layers 7 are welded together, the particles 8 being enclosed between the said layers.

In particular, the peripheries of the at least two layers 7 of the upstream structure 6 are welded, for example, by ultrasound. This construction avoids the loss of particles during the manufacture of the filtration unit 1, in particular during the manipulation of the various layers in order to stack them.

According to a variant, the different layers 7 forming the upstream structure are cut and welded in a single step by means of an ultrasonic welding and cutting appliance.

According to the invention and as illustrated in FIG. 2, the filtration unit 1 comprises, downstream of the upstream structure 6, a downstream structure 9 for retaining the particles 8 formed from at least one layer of porous material 10.

This layer of porous material 10 has a mean pore diameter less than or equal to the diameter D, in particular strictly less than the diameter D.

This downstream structure 9 has at least two functions: the first is to prevent any leakage of particles from the filtration unit. This is because, as the layers 7 framing the particles 8 are produced from non-woven material, the pore diameter of these layers 7 varies over a range. It then happens that the particles 8 pass through the largest pores in the layers 7 of non-woven material.

For example, the size of the particles 8 having an affinity for the prion protein varies between 20 and 150 μm, in particular 40-90 μm and with a mean diameter of 65 μm or 40-140 μm with a mean diameter of 90 μm. The layers 7 between which the particles 8 are interposed have a mean diameter of 12 μm and varies between 7 μm and 40 μm. Thus, it is possible for certain small particles 8 to pass through the largest pores of the layers 7 of non-woven material, causing the particles 8 to pass into the filtered biological fluid.

Where the filtered biological fluid must be reinjected into a patient, it is necessary to prevent the passage of particles into the filtrate. It is the downstream structure 9 that reduces the risk of the particles passing into the filtrate.

The second function of the downstream layer is to regulate the flow of fluid at the outlet orifice 4 from the filtration unit 1.

For example, the layer of porous material 10 of the downstream structure 9 is of the non-woven type.

Other examples of types of porous materials useful for the downstream structure are membranes, woven materials or grilles.

The porosity of the downstream structure 9 depends not only on the size of the particles 8 but also for example on its nature and the porosity of the layers 7 of the upstream structure 6.

In particular, if the layers 7 of the upstream structure 6 framing the particles have a mean pore diameter greater than 8 μm, the mean pore diameter of the layer of porous material 10 of the downstream structure 9 is less than or equal to 8 μm.

In particular, the mean diameter of the pores of the porous material 10 of the downstream structure 9 is less than 10 μm.

As illustrated in FIG. 2, the filtration unit 1 comprises a filtering medium that, in addition to the upstream and downstream structures 6, 9, comprises a pre- and/or post-filter 14, 15.

These pre- and/or post-filters 14, 15 are identical or different and produced, for example, from a non-woven porous material.

The materials forming the layers of filtering medium 5 are chosen, for example, from the group comprising polymers or copolymers based on polypropylene, polyester, polyamide, high or low density polyethylene, polyurethane, polyvinylidene fluoride, polyvinylpyrrolidone and derivatives thereof.

These polymeric products are not generally hydrophilic naturally and must be treated by physical and/or chemical methods in order to confer on them the said hydrophilic properties necessary for the filtration of blood or blood components.

Such polymers made hydrophilic by physical and/or chemical treatment are available on the market.

According to a second aspect of the invention, a description is given below of a pouch system 16 for the selective elimination of a target substance of a biological fluid such as blood or a blood component.

Figure 8:
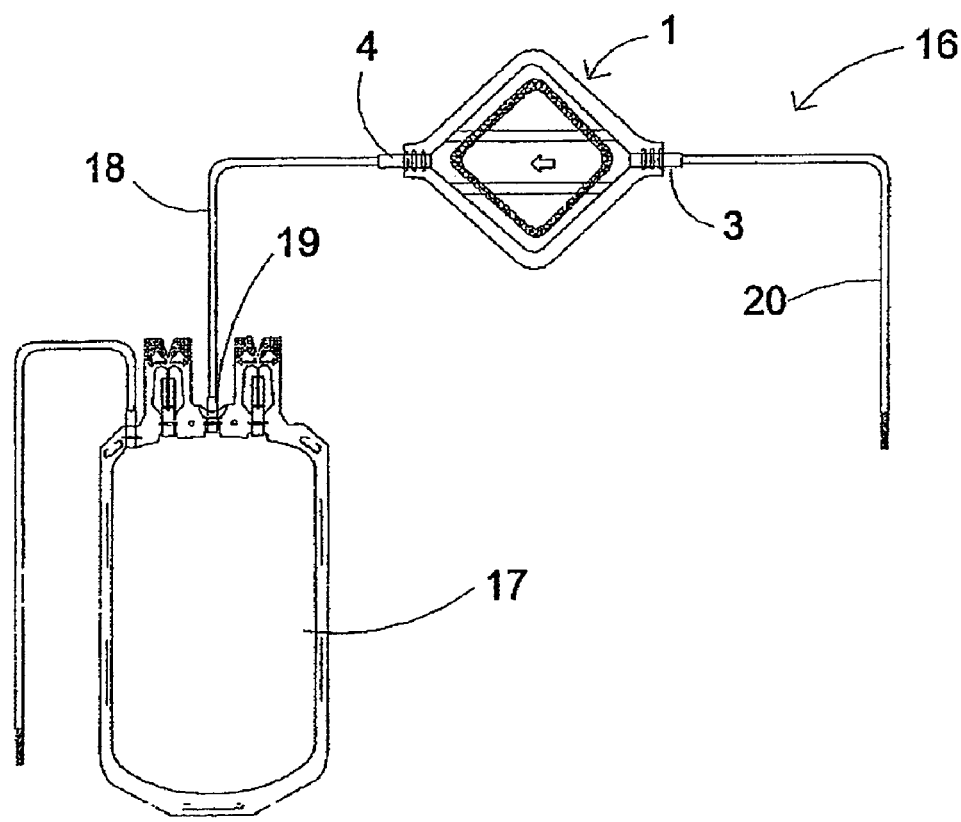
FIG. 8 schematically depicts a pouch system according to the invention comprising a filtration unit.

According to FIG. 8, the pouch system comprises a pouch for collecting the filtrates 17 connected by means of a tube 18 and at an inlet orifice 19 to an outlet orifice 4 of a filtration unit 1 as described above.

In addition the pouch system comprises a tube 20 connected to the inlet orifice of the filtration unit 1.

In use, a pouch containing the fluid to be filtered is connected to the tube 20, for example by means of a sterile connection. Then the fluid to be filtered is allowed to flow by gravity through the filtration unit 1 and the filtered fluid free from the target substance is connected in the filtrate collecting pouch 17.

According to another embodiment, the filtration unit is integrated in a so-called closed pouch system allowing the taking off of the whole blood and its subsequent treatment in order to eliminate the target substance from the whole blood or one of its components.

The invention claimed is:

1. A filtration unit for the selective elimination of a target substance from a biological fluid comprising an external envelope comprising at least one inlet orifice and at least one outlet orifice between which the biological fluid to be filtered flows in one direction, wherein the external envelope encloses a filtering medium comprising, stacked from upstream to downstream:

an upstream structure for eliminating at least the target substance comprising a stack of two or more layers that are arranged to allow the flow of fluid through the layers in one direction comprising a non-woven material having pores with a first mean diameter, and particles interposed between at least some of the layers so as to form at least one sandwich, wherein the particles have an affinity for the target substance and a second mean diameter that is greater than the first mean diameter, and wherein at least two layers are welded together at their periphery and at a plurality of separate welding points so as to retain the distribution of at least a plurality of the particles interposed between the layers; and a downstream structure for retaining the particles comprising at least one layer of porous material having pores with a third mean diameter, wherein the third mean diameter is less than or equal to the first mean diameter.

2. The filtration unit according to claim 1, wherein the first mean diameter is greater than or equal to 8 μm.

3. The filtration unit according to claim 1, wherein the third mean diameter is less than the first mean diameter.

4. The filtration unit according to claim 1, wherein the layers of the upstream structure are arranged so as to eliminate, by adsorption, filtration, or a combination thereof, at least part of the target substance from the biological fluid.

5. The filtration unit according to claim 4, wherein the layers of the upstream structure are arranged so as to eliminate, by adsorption, filtration, or a combination, at least one other component of the biological fluid.

6. The filtration unit according to claim 1, wherein the particles are capable of bonding by affinity to at least one infectious agent.

7. The filtration unit according to claim 6, wherein the infectious agent is at least one selected from the group consisting of: a virus, bacterium, parasite, fungus, prion protein, an exogenous inactivation substance, and a combination thereof.

8. The filtration unit according to claim 1, wherein the particles comprise balls of resin with a diameter between 20 and 150 μm.

9. The filtration unit according to claim 1, wherein the quantity of particles between two layers is between 4 and 10 mg/cm$^2$.

10. The filtration unit according to claim 1, wherein the porous material is of the non-woven type.

11. The filtration unit according to claim 1, wherein the third mean diameter is less than 10 μm.

12. The filtration unit according to claim 1, wherein the filtering medium further comprises at least one selected from the group consisting of a pre-filter, a postfilter, or a combination thereof.

13. A pouch system for the selective elimination of a target substance from a biological fluid such as blood or a blood component comprising a pouch for collecting the filtrate, wherein the pouch is connected by means of a tube and at an inlet orifice to an outlet orifice of a filtration unit that comprises a filtering medium comprising, stacked from upstream to downstream:

an upstream structure for eliminating at least the target substance comprising a stack of two or more layers that are arranged to allow the flow of fluid through the layers in one direction comprising a non-woven material having pores with a first mean diameter, and particles interposed between at least some of the layers so as to form at least one sandwich, wherein the particles have an affinity for the target substance and a second mean diameter that is greater than the first mean diameter, and wherein at least two layers are welded together at their periphery and at a plurality of separate welding points so as to retain the distribution of at least a plurality of the particles interposed between the layers; and a downstream structure for retaining the particles comprising at least one layer of porous material having pores with a third mean diameter, wherein the third mean diameter is less than or equal to the first mean diameter.

14. The filtration unit according to claim 1, wherein the layers of the upstream structure and the particles are arranged so as to form more than one sandwich.

15. The filtration unit according to claim 14, wherein one or more intermediate layers of porous material are interposed between the layers forming the one or more sandwiches.

16. The filtration unit according to claim 1, wherein the particles comprise adsorbent particles selected from the group consisting of activated carbon, aluminum oxide, silica, polystyrene, polymethyl methacrylate, and a combination thereof.

17. The filtration unit according to claim 1, wherein the quantity of particles between two layers is between 4 and 40 mg/cm$^2$.

18. The filtration unit according to claim 1, wherein at least a plurality of the particles are fixed to at least one layer.

19. The filtration unit according to claim 1, wherein the non-woven material comprises at least one material selected from the group consisting of: polypropylene, polyester, polyamide, polyethylene, polyurethane, polyvinylidene fluoride, polyvinylpyrrolidone, derivates thereof, and a combination thereof.

20. The filtration unit according to claim 19, wherein the non-woven material is hydrophilic.

* * * * *